US012805720B2

(12) United States Patent
Timonen et al.

(10) Patent No.: US 12,805,720 B2
(45) Date of Patent: Nov. 24, 2026

(54) TIME-MULTIPLEXED EYE TRACKING

(71) Applicant: Pixieray Oy, Espoo (FI)

(72) Inventors: Juha Timonen, Kauniainen (FI); Ville Miettinen, Helsinki (FI); Klaus Melakari, Espoo (FI)

(73) Assignee: Pixieray Oy, Espoo (FI)

( * ) Notice: Subject to any disclaimer, the term of this patent is extended or adjusted under 35 U.S.C. 154(b) by 342 days.

(21) Appl. No.: 18/517,611

(22) Filed: Nov. 22, 2023

(65) Prior Publication Data

US 2025/0160639 A1 May 22, 2025

(51) Int. Cl.
*A61B 3/113* (2006.01)
*A61B 3/00* (2006.01)
*A61B 3/14* (2006.01)

(52) U.S. Cl.
CPC ............ *A61B 3/113* (2013.01); *A61B 3/0025* (2013.01); *A61B 3/14* (2013.01)

(58) Field of Classification Search
CPC ......... A61B 3/113; A61B 3/0025; A61B 3/14; A61B 3/00; G06F 3/013; G06F 3/01
USPC ............... 351/209, 208, 246, 210, 211, 221; 345/207, 214, 156, 157, 167, 162
See application file for complete search history.

(56) References Cited

U.S. PATENT DOCUMENTS

2023/0239586 A1* 7/2023 Agaoglu ................... G06T 7/70 348/78
2024/0085980 A1* 3/2024 Russell .............. G02B 27/0172
2024/0382088 A1* 11/2024 Pai ......................... A61B 3/113

* cited by examiner

*Primary Examiner* — William R Alexander
*Assistant Examiner* — Kuei-Jen L Edenfield
(74) *Attorney, Agent, or Firm* — ZIEGLER IP LAW GROUP, LLC.

(57) ABSTRACT

Disclosed is a time-multiplexed eye-tracking system with a first set of light emitters and second set of light emitters that are to be employed to emit light beams towards first eye and second eye of user, respectively; first set of light sensors and second set of light sensors that are to be employed to sense reflections of the light beams; and processor(s) communicably coupled to first and second set of LS, wherein processor(s) is configured to: control first and second set of LS to operate in time-multiplexed manner; process sensor data, collected by first set of LS at first time instant, to determine gaze direction of first eye at first time instant; and process sensor data, collected by second set of LS at second time instant, to determine gaze direction of second eye at second time instant.

12 Claims, 2 Drawing Sheets

TIME-MULTIPLEXED EYE TRACKING

TECHNICAL FIELD

The present disclosure relates to time-multiplexed eye-tracking systems. Moreover, the present disclosure relates to methods implemented by time-multiplexed eye-tracking systems.

BACKGROUND

Eye examinations are conventionally used to screen visual acuity of eyes, and are useful for maintaining health of the eyes and overall well-being. In such eye examinations, the visual acuity of the eyes is screened by tracking the eyes of a person. Such tracking of the eyes is used to determine an eye condition and/or investigate cognitive processes. Examples of the eye conditions may be glaucoma, cataracts, diabetic retinopathy, and similar. Examples of the cognitive processes may be attentiveness, perception, memory, and similar, of the person. Conventionally, tracking both the eyes of the individual at the same time instant is a traditional way of implementing the eye tracking. This provides a potential benefit of easy correlation between data procured from both the eyes of the user. This correlated data can then be used to improve an accuracy of said correlation data.

However, conventional eye-tracking systems that are used for tracking the eyes has several limitations associated herewith. Typically, sampling speed during eye tracking is an important parameter, in order to reliably record the movements of the eye. This requires the conventional eye-tracking system to record the movements of the eye at high sampling rate (i.e., the movement of the eyes are recorded at a high frequency). While the conventional eye-tracking systems support high speed of sampling, however, it requires hardware to withstand the high sampling rate, which is costly and consumes a lot of power. Typically, for recording the movements of the eye at high sampling rate, multiple cameras and multiple sensors are used. However, the multiple cameras and the multiple sensors generate a lot of data, and processing the data is power-intensive.

Therefore, in light of the foregoing discussion, there exists a need to overcome the aforementioned drawbacks.

SUMMARY

The aim of the present disclosure is to provide a time-multiplexed eye-tracking system, and a method implemented by the time-multiplexed eye-tracking system to facilitate alternate tracking of the first eye and the second eye. The aim of the present disclosure is achieved by time-multiplexed eye-tracking systems, and methods implemented by the time-multiplexed eye-tracking system as defined in the appended independent claims to which reference is made to. Advantageous features are set out in the appended dependent claims.

Throughout the description and claims of this specification, the words “comprise”, “include”, “have”, and “contain” and variations of these words, for example “comprising” and “comprises”, mean “including but not limited to”, and do not exclude other components, items, integers or steps not explicitly disclosed also to be present. Moreover, the singular encompasses the plural unless the context otherwise requires. In particular, where the indefinite article is used, the specification is to be understood as contemplating plurality as well as singularity, unless the context requires otherwise.

DETAILED DESCRIPTION OF EMBODIMENTS

Figure 1:
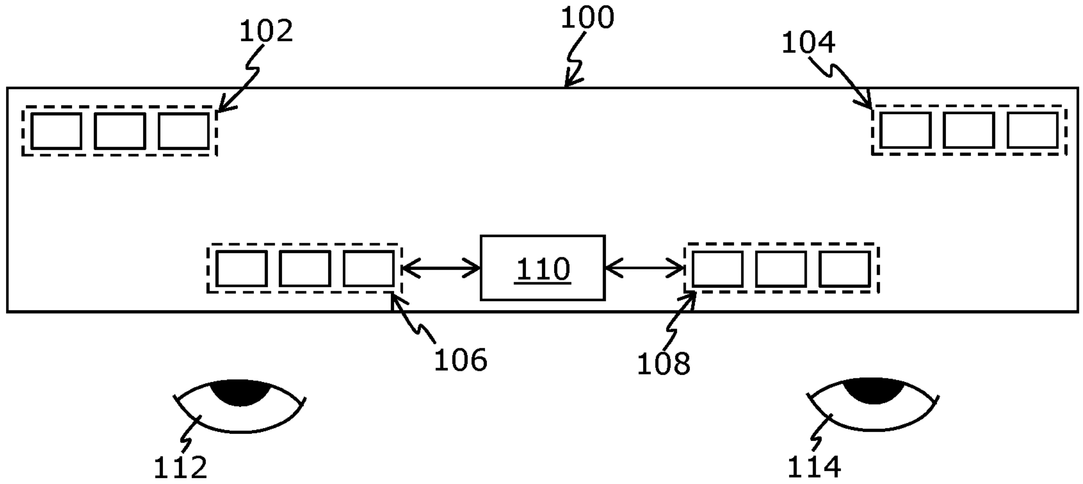
FIG. 1 illustrates a block diagram of an architecture of a time-multiplexed eye-tracking system, in accordance with an embodiment of the present disclosure.

The following detailed description illustrates embodiments of the present disclosure and ways in which they can be implemented. Although some modes of carrying out the present disclosure have been disclosed, those skilled in the art would recognize that other embodiments for carrying out or practising the present disclosure are also possible.

In a first aspect, the present disclosure provides a time-multiplexed eye-tracking system comprising:

- a first set of light emitters and a second set of light emitters that are to be employed to emit light beams towards a first eye and a second eye of a user, respectively;
- a first set of light sensors and a second set of light sensors that are to be employed to sense reflections of the light beams off a surface of the first eye and a surface of the second eye, respectively; and
- at least one processor communicably coupled to the first set of light sensors and the second set of light sensors, wherein the at least one processor is configured to:
  - control the first set of light sensors and the second set of light sensors to operate in a time-multiplexed manner;
  - process sensor data, collected by the first set of light sensors at a first time instant, to determine a gaze direction of the first eye at the first time instant; and
  - process sensor data, collected by the second set of light sensors at a second time instant, to determine a gaze direction of the second eye at the second time instant.

The aforementioned time-multiplexed eye-tracking system is a functional solution for effectively and accurately tracking the first eye and the second eye in the time-multiplexed manner. The first set of light emitters and the first set of light sensors corresponding to the first eye, and the second set of light emitters and the second set of light sensors corresponding to the second eye, are operated in a time-multiplexed manner per eye, which reduces redundancy in the sensor data collected by the first set of light sensors and the second set of light sensors. Beneficially, a given set of light emitters (namely, the first set of light emitters and/or the second set of light emitters) and a given set of light sensors (namely, the first set of light sensors and/or the second set of light sensors) of a given eye (namely the first eye and/or the second eye) of the time-multiplexed eye-tracking system can be used for both eyes of the user (i.e., the first eye and the second eye) to save resources, as both the first eye and the second eye typically move in a conjugated manner. This beneficially saves processing resources, as a sampling rate of the time-multiplexed eye-tracking system is reduced to half of a sampling rate of conventional eye-tracking systems. A synergistic effect of these features is that the time-multiplexed eye-tracking system can be flexibly used to simultaneously track both eyes of the user, or switch between the first eye and the second eye of the user, as per requirement.

In a second aspect, the present disclosure provides a method implemented by a time-multiplexed eye-tracking system comprising a first set of light emitters, a second set of light emitters, a first set of light sensors, a second set of light sensors, and at least one processor, wherein the method comprises:

controlling the first set of light sensors and the second set of light sensors to operate in a time-multiplexed manner;

processing sensor data, collected by the first set of light sensors at a first time instant, to determine a gaze direction of the first eye at the first time instant; and processing sensor data, collected by the second set of light sensors at a second time instant, to determine a gaze direction of the second eye at the second time instant.

The aforementioned method implemented by the time-multiplexed eye-tracking system provides a functional solution for tracking of the first eye and the second eye, by effectively and accurately tracking the first eye and the second eye in the time-multiplexed manner. Herein, by controlling the first set of light sensors and the second set of light sensors in a time-multiplexed manner per eye, redundancy while procuring the sensor data is reduced significantly. The aforementioned method beneficially saves processing resources by implementing the given set of light emitters and the given set of light sensors for both the eyes of the user, as both the first eye and the second eye typically move in a conjugated manner. Hence, a sampling rate of the time-multiplexed eye-tracking system is reduced to half of a sampling rate of conventional eye-tracking systems. A synergistic effect of these features is that the aforementioned method can be used to simultaneously track both eyes of the user, or switch between the first eye and the second eye of the user, as per requirement.

Throughout the present disclosure, the term "time-multiplexed eye tracking system" refers to a system that is used for at least tracking the gaze directions of the user's eyes, in a time-multiplexed manner (i.e., in a time-alternating manner). In this regard, an available time is divided into time slots in a discrete manner, and assigns a particular time slot to at least track the gaze directions of the user's eyes. Optionally, the time-multiplexed eye-tracking system is implemented as an internal component of an optical apparatus or a head-mounted display (HMD) device, as an external component of an optical apparatus or an HMD device, or as an external system arranged on a surface. Herein, the term "optical apparatus" refers to an apparatus that is to be worn over the eyes of the user. Examples of the optical apparatus include, but are not limited to, a pair of glasses, a pair of sunglasses, smart glasses, and a head-mounted display. Moreover, the term "head-mounted display" device refers to a specialized equipment that is configured to present an extended-reality (XR) environment to the user when said HMD device, in operation, is worn by the user on his/her head. The HMD device is implemented, for example, as an XR headset, a pair of XR glasses, and the like, that is operable to display a visual scene of the XR environment to the user. The term "extended-reality" encompasses virtual reality (VR), augmented reality (AR), mixed reality (MR), and the like.

Throughout the present disclosure, the term "light emitter" refers to an element that produces or emits light beams. In other words, a given set of light emitters (namely, the first set of light emitters and/or the second set of light emitters), when activated, emits light. The given set of light emitters comprises a plurality of light-emitters, wherein a given light-emitter comprises one of: an infrared light-emitting diode, a visible-light emitting diode. Herein, the term "light beams" refers to concentrated and directional flow of light towards a given eye (namely, the first eye and/or the second eye). The first set of light emitters are arranged corresponding to the first eye of the user, and the second set of light emitters are arranged corresponding to the second eye of the user.

Throughout the present disclosure, the term "light sensor" refers to a device that is used to detect and/or measure the light beams that are reflected from the surface of the given eye. Data received from the light sensors is used to at least one of: determine a direction of gaze of the given eye at a given time instant (namely, the first time instant and/or the second time instant), follow the direction of the gaze of the given eye at the given time instant, monitor features of the given eye at the given time instant, when the user uses the time-multiplexed eye-tracking system. The features may comprise the reflections of the light beams reflecting off the surface of the first eye, reflections of the light beams reflecting off the surface of the second eye, a relative position of a pupil of the first eye with respect to the reflections of the light beams emitted by the first set of light emitters, a relative position of a pupil of the second eye with respect to the reflections of the light beams emitted by the second set of light emitters. The first set of light sensors and the second set of light sensors are in use when the time-multiplexed eye-tracking system, in operation, is used by the user. The first set of light sensors is arranged corresponding to the first eye, and the second set of light sensors is arranged corresponding to the second eye. Examples of the light sensors may include, but are not limited to, a photoresistor, a photodiode, a phototransistor, an ultraviolet sensor, and an infrared sensor.

Notably, the sensor data of the first eye at a first time instant and the sensor data of the second eye at a second time instant is collected by the first set of light sensors and the second set of light sensors, respectively, at a particular sampling rate (as is described later) within time slots (as is described later), throughout an operation of the time-multiplexed eye-tracking system and sent to the at least one processor. In some implementations, the first time instant and the second time instant are consecutive instants of time with no programmable delay in between the two aforesaid instants of time. In other implementations, the first time instant and the second time instant are consecutive instants of time with a programmable delay in between the two aforesaid instants of time.

It will be appreciated that the at least one processor is communicably coupled to the first set of light sensors and the second set of light sensors. The at least one processor is optionally coupled to the first set of light emitters and the second set of light emitters. The at least one processor could be implemented as any one of: a microprocessor, a microcontroller, or a controller. As an example, the at least one processor could be implemented as an application-specific integrated circuit (ASIC) chip, or a reduced instruction set computer (RISC) chip.

Optionally, the at least one processor is configured to control the first set of light emitters and the second set of light emitters to operate in the time-multiplexed manner. In this regard, the at least one processor is configured to alternately control the first set of light emitters and the second set of light emitters in different time slots, in a predefined sequence or pattern over time. During each time slot, one of the first set of light emitters or the second set of light emitters is activated, while another of the second set of light emitters or the first set of light emitters is inactive or deactivated. A technical effect of operating the first set of light emitters and the second set of light emitters in a time-multiplexed manner is that it facilitates in reduction of interference between the first set of light emitters and the second set of light emitters, optimal distribution of processing resources, and conservation of energy of the light emitters.

Optionally, the time-multiplexed eye-tracking system further comprises a servo-controller, wherein the servo-controller is communicably coupled to the first set of light emitters and the second set of light emitters, and the servo-controller is configured to control the first set of light emitters and the second set of light emitters in a time-multiplexed manner. Herein, the term "servo-controller" refers to a hardware, software, firmware, or a combination of these, for alternately dynamically controlling an operation of the first set of light emitters and the second set of light emitters in different time slots. During each time slot, one of the first set of light emitters or the second set of light emitters is activated, while another of the second set of light emitters or the first set of light emitters is inactive or deactivated. In some implementations, the servo-controller is implemented as a processor of the time-multiplexed eye-tracking system. In other implementations, the time-multiplexed eye-tracking system comprises an external computing device that is communicably coupled with the first set of light emitters and the second set of light emitters; in such a case, the servo-controller is implemented as a processor of the external computing device. In such a case, at least a part of all the aforementioned processing tasks of the servo-controller is performed at the external computing device. A technical effect of using the servo-controller to control the first set of light emitters and the second set of light emitters in a time-alternate manner is that, it enables the light beams to be accurately directed towards the given eye and ensure that the light beams emitted can be reflected from a surface of the given eye.

The at least one processor is configured to control an operation of the first set of light sensors and an operation of the second set of light sensors in the time-alternating manner. In this regard, the at least one processor is configured to alternately control the first set of light sensors and the second set of light sensors in different time slots, in another predefined sequence or another pattern over time. During each time slot, one of the first set of light sensors or the second set of light sensors is activated, while another of the second set of light sensors or the first set of light sensors is inactive or deactivated. The sensor data is collected to capture at least one of: a movement of the first eye and/or the second eye, a saccade of the first eye and/or the second eye, a change in appearance of the pupil in the first eye and/or the second eye, a change in intensity and/or brightness of the light beams. A technical effect of collecting the sensor data by the first set of light sensors and the second set of light sensors is to determine a mapping between the sensor data and the direction of the gaze of the given eye.

Optionally, when controlling the first set of light sensors and the second set of light sensors to operate in the time-multiplexed manner, the at least one processor is configured to send instructions to the first set of light sensors and the second set of light sensors, wherein the instructions indicate at least one of:

- time slots in which the first set of light sensors are to sense the reflections of the light beams,
- time slots in which the second set of light sensors are to sense the reflections of the light beams,
- a sampling rate at which the first set of light sensors are to sense the reflections of the light beams,
- a sampling rate at which the second set of light sensors are to sense the reflections of the light beams.

A technical effect of sending instructions to the first set of light sensors and the second set of light sensors is to reduce an effort required for processing by half. In this regard, the instructions are sent from the at least one processor to the first set of light sensors and the second set of light sensors, in order to control the first set of light sensors and the second set of light sensors in a time-multiplexed manner. The instructions indicate respective time slots for the first set of light sensors and the second set of light sensors to prevent simultaneous activation of the first set of light sensors and the second set of light sensors. Herein, the term "time slot" refers to a discrete time period (namely, a duration of time, a length of time) in which the given set of light sensors are to be activated to sense the reflections of the light beams. The time slots in which the first set of light sensors are to sense the reflections of the light beams could overlap, with a time offset (as will be described later) in between, with the time slots in which the second set of light sensors are to sense the reflections of the light beams.

The first time instant at which the first set of light sensors collect the sensor data, must be present within the time slot in which the first set of light sensors are to sense the reflections of the light beams. The second time instant at which the second set of light sensors collect the sensor data, must be present within the time slot in which the second set of light sensors are to sense the reflections of the light beams. The time slots may be expressed in terms of millisecond (ms), minute (min), or similar. Optionally, the time slots can be represented as a graphical representation (for example, such as a square waveform graph), a table, a text file. The term "sampling rate" refers to reflections sensed by the first set of light sensors and the second set of light sensors, per unit time in respective time slot. The sampling rate may be expressed in terms of hertz (Hz). The sampling rate is greater than twice a rate at which a phenomena (for example, such as a saccade, a movement, an acceleration of the given eye) occurs.

In some implementations, the first eye and/or the second eye are fixated at a gaze point. Herein, the term "gaze point" refers to a point in a real-world environment in which the gaze of the user is focused, i.e., at which the gaze directions of the first eye and the second eye converge. In this regard, the at least one processor is configured to control the given set of light sensors in such a manner that the given set of light sensors senses the reflections of the light beams off the surface of the given eye at least twice per unit time in the time slots. When it is determined that there is no movement of the first eye and/or the second eye, the sensor data is processed to determine the gaze direction of the first eye and/or the second eye.

In other implementations, the first eye and/or the second eye are constantly moving with respect to a moving object (for example, such as the first eye and the second eye may be in smooth pursuit, wherein the first eye and the second eye may be fixated at a moving object in the real-world environment). In this regard, the at least one processor is configured to control the given set of light sensors in such a manner that the sampling rate is higher than a speed of the movement of the given eye. A technical effect of controlling the given set of light sensors in such a manner is that such controlling can be used to model at least one of: a tremor, a stability, an acceleration, a peak velocity, of the first eye and/or the second eye. In a first example, if the first eye and/or the second eye is sampled every 10 ms (in other words, the first eye and/or the second eye moves at most four times per second), the sampling rate may be two, wherein the reflections off the surface of the first eye and/or the surface of the second eye may be sensed by the first set of light sensors and/or the second set of light sensors every 5 ms, wherein it may be detected that there is movement of the first eye and/or the second eye.

In yet other implementations, the first eye and/or the second eye accelerate, in which case the time-multiplexed eye-tracking system can be used to determine the next gaze point, by determining the gaze direction of the first eye and/or the second eye. In this regard, the at least one processor is configured to control the given set of light sensors in such a manner that the sampling rate is higher than an acceleration of the given eye. Continuing in reference with the first example, the sampling rate may be three, wherein the reflections off the surface of the first eye and/or the surface of the second eye may be sensed by the first set of light sensors and/or the second set of light sensors every 3.3 ms.

In still other implementations, saccade of the first eye and/or saccade of the second eye is to be determined using the time-multiplexed eye-tracking system. In this regard, the at least one processor is configured to control the given set of light sensors in such a manner that the sampling rate is higher than the saccade of the given eye. For example, the saccade of the first eye and/or the second eye may take 20 ms. The sampling rate may be two, wherein the reflections off the surface of the first eye and/or the surface of the second eye may be sensed by the first set of light sensors and/or the second set of light sensors every 10 ms.

In yet still other implementations, micro saccade of the first eye and/or saccade of the second eye is to be determined using the time-multiplexed eye-tracking system. In this regard, the at least one processor is configured to control the given set of light sensors in such a manner that the sampling rate is higher than the micro saccade of the given eye. The micro saccade, a momentary position of the given eye is determined, as in micro saccade-level, the given eye is constantly moving. Optionally, post-saccade tremor is also collected as sensor data by the first set of light sensors and/or the second set of light sensors, as gaze direction of the first eye and/or the second eye will continuously change therein.

In some embodiments, a difference between the sensor data collected by the first set of light sensors at the first time instant and the sensor data collected by the second set of light sensors at the second time instant, is used as a trigger condition to decrease the sampling rate of the first set of light sensors and/or the second set of light sensors from a current sampling rate. In other embodiments, a position of reflections is oversampled, and spatial accuracy is optimised in expense of temporal accuracy.

The sensor s set of light sensors at the second time instant, is processed by the at least one processor. In this regard, the at least one processor is configured to employ at least one of: an image processing algorithm, a feature extraction algorithm, a data processing algorithm. Other suitable algorithm(s) can also be employed, depending on a type of the sensor data. A technical effect of processing the sensor data to determine the gaze direction of the given eye at the given time instant is to track the given eye accurately at the given time instant.

Optionally, the at least one processor is configured to:

estimate a gaze direction of the second eye at the first time instant, based on the determine gaze direction of the first eye at the first time instant and at least one previous gaze direction of the second eye at a previous time instant; and estimate a gaze direction of the first eye at the second time instant, based on the determine gaze direction of the second eye at the second time instant and at least one previous gaze direction of the first eye at a previous time instant.

In this regard, the gaze direction of the second eye at the first time instant is estimated based on a correlation of the gaze direction of the first eye at the first time instant and by taking into account the at least one previous gaze direction of the second eye at the previous time instant. The at least one previous gaze direction of the second eye is used to determine how the gaze direction of the second eye is likely to change relative to the gaze direction of the first eye of the user. From the gaze direction of the first eye, an angular distance between the gaze direction of the first eye and an optical centre of the gaze point is determined. This angular distance is applied to the at least one previous gaze direction of the second eye, to estimate the gaze direction of the second eye at the first time instant. This is applicable in typical cases of conjugated eye movements, in which both the first eye and the second eye move together in the same direction by a same amount.

The gaze direction of the first eye at the second time instant is estimated based on a correlation of the gaze direction of the second eye at the second time instant and by taking into account the at least one previous gaze direction of the first eye at the previous time instant. It will be appreciated that the previous time instant of the at least one previous gaze direction of the first eye may not be the same as the previous time instant of the at least one previous gaze direction of the second eye, because of time-multiplexing. However, in an instance where a previously-estimated gaze direction of the first eye is used, the previous time instant of the at least one previous gaze direction of the first eye may be same as the previous time instant of the at least one previous gaze direction of the second eye. The at least one previous gaze direction of the first eye is used to determine how the gaze direction of the first eye is likely to change relative to the gaze direction of the second eye of the user. From the gaze direction of the second eye, an angular distance between the gaze direction of the second eye and an optical centre of the gaze point is determined. This angular distance is applied to the at least one previous gaze direction of the first eye, in order to estimate the gaze direction of the first eye at the second time instant. Herein, the at least one previous gaze direction of the second eye and/or the at least one previous gaze direction of the first eye at respective previous time instants help to distinguish between a situation where the first eye and the second eye are moving synchronously (for example, while reading), and another situation where the first eye and the second eye are moving in opposite directions (for example, when converging to see a nearby object).

A technical effect of estimating the gaze direction of the second eye at the first time instant and estimating the gaze direction of the first eye at the second time instant is that it enables an accurately analyse coordination of gaze between the first eye and the second eye which can provide insights into natural eye movement patterns and behaviours.

Optionally, when controlling the first set of light sensors and the second set of light sensors to operate in the time-multiplexed manner, the at least one processor is configured to employ a time offset between the first time instant and the second time instant that lies within a predefined threshold from 50 percent of a time interval between two consecutive time instants when the sensor data is collected from any one of the first set of light sensors and the second set of light sensors. Herein, the term "time offset" refers to a difference between the first time instant and the second time instant while controlling any one of the first set of light sensors or the second set of light sensors. The time offset lies within the predefined threshold from exactly halfway between two consecutive time instants. In other words, the time offset is centred within the time interval between the first time instant and the second time instant. A technical effect of employing the time offset between the first time instant and the second time instant is that this facilitates precise control and coordination in the time-multiplexed manner.

Optionally, the predefined threshold is 50 percent of the time interval between the two consecutive time instants when the sensor data is collected from any one of the first set of light sensors and the second set of light sensors. Alternatively, optionally, the predefined threshold lies in a range from 0 percent to 50 percent of the time interval between the two consecutive time instants when the sensor data is collected from any one of the first set of light sensors and the second set of light sensors. The predefined threshold lies in a range from 0, 5, 10, 20, or 40 percent to 15, 25, 35, 45, or 50 percent. Yet alternatively, optionally, the predefined threshold lies in a range from 50 percent to 100 percent of the time interval between the two consecutive time instants when the sensor data is collected from any one of the first set of light sensors and the second set of light sensors. The predefined threshold lies in a range from 50, 55, 60, 70, or 90 percent to 65, 75, 85, 95, 100 percent.

Optionally, when controlling the first set of light emitters and the second set of light emitters to operate in the time-multiplexed manner, the at least one processor is configured to send instructions to the first set of light emitters and the second set of light emitters, wherein the instructions indicate at least one of:

- time slots in which the first set of light emitters are to emit the light beams,
- time slots in which the second set of light emitters are to emit the light beams,
- a rate at which the first set of light emitters are to emit the light beams,
- a rate at which the second set of light emitters are to emit the light beams.

A technical effect of sending instructions to the first set of light emitters and the second set of light emitters is to reduce interference between the light beams emitted by the first set of light emitters and the second set of light emitters, thereby ensuring that they emit the light beams at required time instants when collecting the sensor data. The time slots in which the first set of light emitters are to emit the light beams can coincide with the time slots in which the first set of light sensors are to sense the reflections of the light beams. Similarly, the time slots in which the first set of light emitters are to emit the light beams can coincide with the time slots in which the first set of light sensors are to sense the reflections of the light beams. The "rate" at which the first set of light emitters are to emit the light beams is a frequency with which the light beams are emitted by the given set of light emitters. The rate may be expressed in terms of hertz (Hz). For example, if the instructions indicate a rate of 50 Hz for the first set of light emitters, it means that these emitters emit the light beams 50 times per second.

The present disclosure also relates to the second aspect as described above. Various embodiments and variants disclosed above, with respect to the aforementioned first aspect, apply mutatis mutandis to the second aspect.

Optionally, the method comprises:

- estimating a gaze direction of the second eye at the first time instant, based on the determine gaze direction of the first eye at the first time instant and at least one previous gaze direction of the second eye at a previous time instant; and
- estimating a gaze direction of the first eye at the second time instant, based on the determine gaze direction of the second eye at the second time instant and at least one previous gaze direction of the first eye at a previous time instant.

Optionally, at the step of controlling the first set of light sensors and the second set of light sensors to operate in a time-multiplexed manner, the method comprises employing a time offset between the first time instant and the second time instant that lies within a predefined threshold from 50 percent of a time interval between two consecutive time instants when the sensor data is collected from any one of the first set of light sensors and the second set of light sensors.

Optionally, at the step of controlling the first set of light sensors and the second set of light sensors to operate in the time-multiplexed manner, the method comprises sending instructions to the first set of light sensors and the second set of light sensors, wherein the instructions indicate at least one of:

- time slots in which the first set of light sensors are to sense the reflections of the light beams,
- time slots in which the second set of light sensors are to sense the reflections of the light beams,
- a sampling rate at which the first set of light sensors are to sense the reflections of the light beams,
- a sampling rate at which the second set of light sensors are to sense the reflections of the light beams.

Optionally, the method comprises controlling the first set of light emitters and the second set of light emitters to operate in the time-multiplexed manner.

Optionally, at the step of controlling the first set of light emitters and the second set of light emitters to operate in the time-multiplexed manner, the method comprises sending instructions to the first set of light emitters and the second set of light emitters, wherein the instructions indicate at least one of:

- time slots in which the first set of light emitters are to emit the light beams,
- time slots in which the second set of light emitters are to emit the light beams,
- a rate at which the first set of light emitters are to emit the light beams,
- a rate at which the second set of light emitters are to emit the light beams.

DETAILED DESCRIPTION OF THE DRAWINGS

Referring to FIG. 1, there is illustrated a block diagram of an architecture of a time-multiplexed eye-tracking system 100, in accordance with an embodiment of the present disclosure. The time-multiplexed eye-tracking system 100 comprises a first set 102 of light emitters, a second set 104 of light emitters, a first set 106 of light sensors, a second set 108 of light sensors, and at least one processor (depicted as a processor 110). The first set 102 of light emitters and the second set 104 of light emitters that are to be employed to emit light beams towards a first eye 112 and a second eye 114 of a user, respectively. The first set 106 of light sensors and the second set 108 of light sensors that are to be employed to sense reflections of the light beams off a surface of the first eye 112 and a surface of the second eye 114, respectively. The processor 110 is communicably coupled to the first set 106 of light sensors and the second set 108 of light sensors. The processor 110 is configured to perform various operations, as described earlier with respect to the aforementioned first aspect.

FIG. 1 is merely an example, which should not unduly limit the scope of the claims herein. A person skilled in the art will recognize many variations, alternatives, and modifications of embodiments of the present disclosure.

Figure 2A:
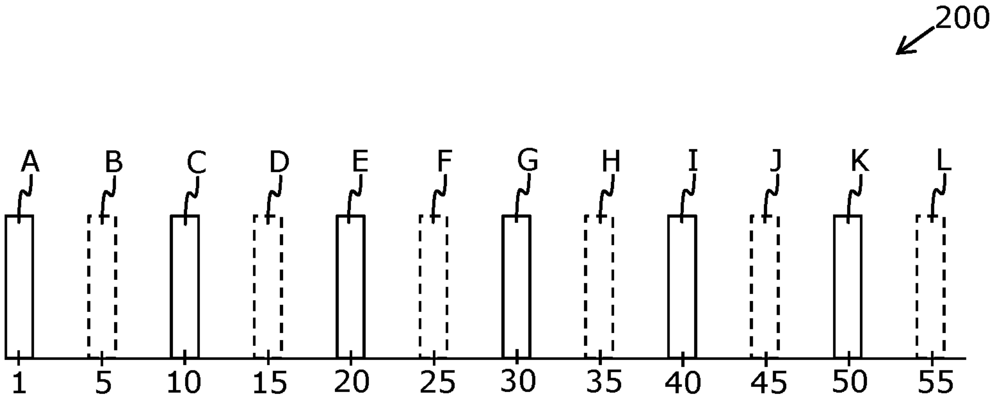
FIGS. 2A and 2B illustrate exemplary graphical representations of controlling the first set of light sensors and the second set of light sensors of FIG. 1, in accordance with an embodiment of the present disclosure.
Figure 2B:
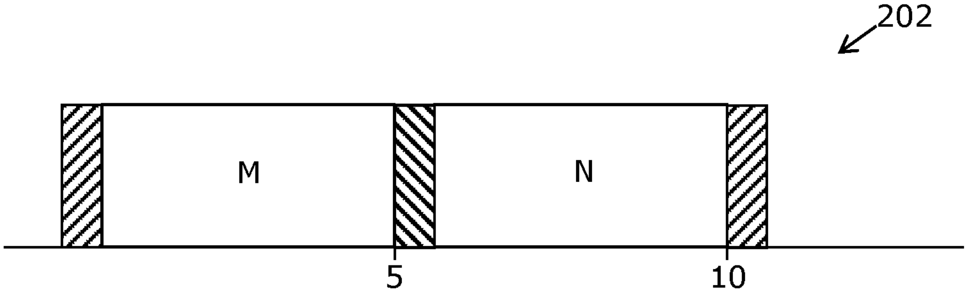

Referring to FIGS. 2A and 2B, there are illustrated exemplary graphical representations 200 and 202 of controlling the first set 106 of light sensors and the second set 108 of light sensors of FIG. 1, in accordance with an embodiment of the present disclosure. In FIGS. 2A-2B, the graphical representations 200 and 202 are in a form of square waveform graphs whose horizontal axis represents time in milliseconds (ms). When controlling the first set 106 of light sensors and the second set 108 of light sensors to operate in the time-multiplexed manner, the processor 110 of FIG. 1 is configured to send instructions to the first set 106 of light sensors and the second set 108 of light sensors. In FIG. 2A, time slots (as depicted by solid-line square waves A, C, E, G, I, and K) in which the first set 106 of light sensors are to sense the reflections of the light beams, time slots (as depicted by dashed-line square waves B, D, F, H, J, and L) in which the second set 108 of light sensors are to sense the reflections of the light beams are illustrated. The time slots A, C, E, G, I, and K for the first set 106 of light sensors are arranged in a time-multiplexed manner with the time slots B, D, F, H, J, and L for the second set 108 of light sensors. These time slots are indicated in the instructions. The sensor data is collected at a first time instant (i.e., at 1 ms) by the first set 106 of light sensors, and the sensor data is collected at a second time instant (i.e., at 5 ms) by the second set 108 of light sensors. In FIG. 2B, time offsets (as depicted by solid-line square waves M and N) are illustrated, wherein the processor 110 is configured to employ the time offsets M-N between the first time instant and the second time instant that lies within a predefined threshold from 50 percent of a time interval between two consecutive time instants when sensor data is collected from any one of the first set 106 of light sensors, as depicted by upward diagonal stripes, and the second set 108 of light sensors, as depicted by downward diagonal stripes. For example, the time offset M lies between the first instant (i.e., at 1 ms) and the second time instant (i.e., at 5 ms) within the predefined threshold from 2.5 ms (i.e., 50 percent of the time interval of 5 ms between the first time instant and the second time instant).

FIGS. 2A-B are merely examples, which should not unduly limit the scope of the claims herein. A person skilled in the art will recognize many variations, alternatives, and modifications of embodiments of the present disclosure.

Figure 3:
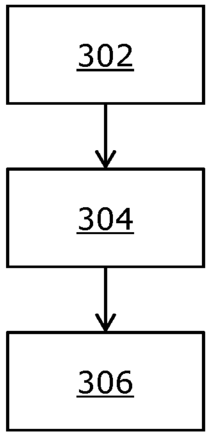
FIG. 3 shows a flowchart illustrating steps of a method implemented by a time-multiplexed eye-tracking system comprising a first set of light emitters, a second set of light emitters, a first set of light sensors, a second set of light sensors, and at least one processor, in accordance with an embodiment of the present disclosure.

Referring to FIG. 3, there is shown a flowchart illustrating steps of a method implemented by a time-multiplexed eye-tracking system comprising a first set of light emitters, a second set of light emitters, a first set of light sensors, a second set of light sensors, and at least one processor, in accordance with an embodiment of the present disclosure. At step 302, the first set of light sensors and the second set of light sensors are controlled to operate in a time-multiplexed manner. At step 304, sensor data, collected by the first set of light sensors at a first time instant, is processed to determine a gaze direction of the first eye at the first time instant. At step 306, sensor data, collected by the second set of light sensors at a second time instant, is processed to determine a gaze direction of the second eye at the second time instant.

The aforementioned steps are only illustrative and other alternatives can also be provided where one or more steps are added, one or more steps are removed, or one or more steps are provided in a different sequence without departing from the scope of the claims herein.

The invention claimed is:

1. A time-multiplexed eye-tracking system comprising:
- a first set of light emitters and a second set of light emitters that are to be employed to emit light beams towards a first eye and a second eye of a user, respectively;
- a first set of light sensors and a second set of light sensors that are to be employed to sense reflections of the light beams off a surface of the first eye and a surface of the second eye, respectively; and
- at least one processor communicably coupled to the first set of light sensors and the second set of light sensors, wherein the at least one processor is configured to:
  - control the first set of light sensors and the second set of light sensors to operate in a time-multiplexed manner;
  - process sensor data, collected by the first set of light sensors at a first time instant, to determine a gaze direction of the first eye at the first time instant;
  - process sensor data, collected by the second set of light sensors at a second time instant, to determine a gaze direction of the second eye at the second time instant;
  - determine a difference between the sensor data collected by the first set of light sensors at the first time instant and the sensor data collected by the second set of light sensors at the second time instant; and
  - decrease a sampling rate of at least one of the first set of light sensors or the second set of light sensors responsive to the determined difference satisfying a trigger condition.

2. The time-multiplexed eye-tracking system of claim 1, wherein the at least one processor is configured to:
- estimate a gaze direction of the second eye at the first time instant, based on the determine gaze direction of the first eye at the first time instant and at least one previous gaze direction of the second eye at a previous time instant; and
- estimate a gaze direction of the first eye at the second time instant, based on the determine gaze direction of the second eye at the second time instant and at least one previous gaze direction of the first eye at a previous time instant.

3. The time-multiplexed eye-tracking system of claim 1, wherein when controlling the first set of light sensors and the second set of light sensors to operate in the time-multiplexed manner, the at least one processor is configured to employ a time offset between the first time instant and the second time instant that lies within a predefined threshold from 50 percent of a time interval between two consecutive time instants when the sensor data is collected from any one of the first set of light sensors and the second set of light sensors.

4. The time-multiplexed eye-tracking system of claim 1, wherein when controlling the first set of light sensors and the second set of light sensors to operate in the time-multiplexed manner, the at least one processor is configured to send instructions to the first set of light sensors and the second set of light sensors, wherein the instructions indicate at least one of:

time slots in which the first set of light sensors are to sense the reflections of the light beams, time slots in which the second set of light sensors are to sense the reflections of the light beams, a sampling rate at which the first set of light sensors are to sense the reflections of the light beams, a sampling rate at which the second set of light sensors are to sense the reflections of the light beams.

5. The time-multiplexed eye-tracking system of claim 1, wherein the at least one processor is configured to control the first set of light emitters and the second set of light emitters to operate in the time-multiplexed manner.

6. The time-multiplexed eye-tracking system of claim 5, wherein, when controlling the first set of light emitters and the second set of light emitters to operate in the time-multiplexed manner, the at least one processor is configured to send instructions to the first set of light emitters and the second set of light emitters, wherein the instructions indicate at least one of:

time slots in which the first set of light emitters are to emit the light beams, time slots in which the second set of light emitters are to emit the light beams, a rate at which the first set of light emitters are to emit the light beams, a rate at which the second set of light emitters are to emit the light beams.

7. A method implemented by a time-multiplexed eye-tracking system comprising a first set of light emitters, a second set of light emitters, a first set of light sensors, a second set of light sensors, and at least one processor, wherein the method comprises:

emitting light beams from the first set of light emitters and the second set of light emitters towards a first eye and a second eye of a user, respectively;

controlling the first set of light sensors and the second set of light sensors to operate in a time-multiplexed manner;

processing sensor data, collected by the first set of light sensors at a first time instant, to determine a gaze direction of the first eye at the first time instant; and processing sensor data, collected by the second set of light sensors at a second time instant, to determine a gaze direction of the second eye at the second time instant;

determining a difference between the sensor data collected by the first set of light sensors at the first time instant and the sensor data collected by the second set of light sensors at the second time instant; and decreasing a sampling rate of at least one of the first set of light sensors or the second set of light sensors responsive to the determined difference satisfying a trigger condition.

8. The method of claim 7, wherein the method comprises:

estimating a gaze direction of the second eye at the first time instant, based on the determine gaze direction of the first eye at the first time instant and at least one previous gaze direction of the second eye at a previous time instant; and estimating a gaze direction of the first eye at the second time instant, based on the determine gaze direction of the second eye at the second time instant and at least one previous gaze direction of the first eye at a previous time instant.

9. The method of claim 7, wherein at the step of controlling the first set of light sensors and the second set of light sensors to operate in a time-multiplexed manner, the method comprises employing a time offset between the first time instant and the second time instant that lies within a predefined threshold from 50 percent of a time interval between two consecutive time instants when the sensor data is collected from any one of the first set of light sensors and the second set of light sensors.

10. The method of claim 7, wherein at the step of controlling the first set of light sensors and the second set of light sensors to operate in the time-multiplexed manner, the method comprises sending instructions to the first set of light sensors and the second set of light sensors, wherein the instructions indicate at least one of:

time slots in which the first set of light sensors are to sense the reflections of the light beams, time slots in which the second set of light sensors are to sense the reflections of the light beams, a sampling rate at which the first set of light sensors are to sense the reflections of the light beams, a sampling rate at which the second set of light sensors are to sense the reflections of the light beams.

11. The method of claim 7, the method comprises controlling the first set of light emitters and the second set of light emitters to operate in the time-multiplexed manner.

12. The method of claim 11, wherein at the step of controlling the first set of light emitters and the second set of light emitters to operate in the time-multiplexed manner, the method comprises sending instructions to the first set of light emitters and the second set of light emitters, wherein the instructions indicate at least one of:

time slots in which the first set of light emitters are to emit the light beams, time slots in which the second set of light emitters are to emit the light beams, a rate at which the first set of light emitters are to emit the light beams, a rate at which the second set of light emitters are to emit the light beams.

* * * * *